United States Patent
Zaima et al.

(10) Patent No.: US 7,611,078 B2
(45) Date of Patent: Nov. 3, 2009

(54) METHOD OF PRODUCING POWERED MEDICINE MULTI-DOSE ADMINISTERING DEVICE AND APPARATUS THEREOF

(75) Inventors: Yasuhiro Zaima, Iwakuni (JP); Masahiko Dohi, Tokyo (JP); Seiji Mochizuki, Iwakuni (JP); Hiroshi Kuroda, Osaka (JP)

(73) Assignee: Teijin Limited, Osaka (JP)

( * ) Notice: Subject to any disclaimer, the term of this patent is extended or adjusted under 35 U.S.C. 154(b) by 1132 days.

(21) Appl. No.: 10/489,662

(22) Filed: Mar. 16, 2004

(65) Prior Publication Data

US 2004/0237276 A1   Dec. 2, 2004

(30) Foreign Application Priority Data

Jul. 16, 2002  (JP)  ............... 2002-207371

(51) Int. Cl.
*F23D 11/10*  (2006.01)

(52) U.S. Cl. ............ 239/418; 604/57; 604/58; 604/73; 128/203.12

(58) Field of Classification Search ............ 604/82–92, 604/93.01, 58, 68–71, 73; 239/418; 128/203.12
See application file for complete search history.

(56) References Cited

U.S. PATENT DOCUMENTS

| | | | | |
|---|---|---|---|---|
| 4,224,979 A | * | 9/1980 | Rosin et al. ............ | 164/130 |
| 4,487,696 A | * | 12/1984 | Ferrara ............ | 210/399 |
| 5,238,153 A | * | 8/1993 | Castillo et al. ........ | 222/189.09 |
| 5,423,216 A | * | 6/1995 | Kitamura et al. ............ | 73/433 |
| 5,605,257 A | * | 2/1997 | Beard ............ | 222/189.09 |
| 5,634,900 A | * | 6/1997 | Makino et al. ............ | 604/58 |
| 6,325,475 B1 | * | 12/2001 | Hayes et al. ............ | 347/2 |
| 6,488,648 B1 | * | 12/2002 | Matsugi et al. ............ | 604/57 |
| 6,601,365 B2 | * | 8/2003 | Arishiro et al. ............ | 53/54 |
| 6,824,080 B2 | * | 11/2004 | Matsugi et al. ............ | 239/418 |

FOREIGN PATENT DOCUMENTS

| | | |
|---|---|---|
| EP | 1 066 849 A1 | 1/2001 |
| JP | 11-33116 A | 2/1999 |
| WO | WO 94/26338 A1 | 11/1994 |
| WO | WO 00/41755 A1 | 7/2000 |
| WO | WO 01/60695 A1 | 8/2001 |
| WO | WO 01/83013 A2 | 11/2001 |
| WO | WO 01/095962 A1 | 12/2001 |
| WO | WO 02/13886 A2 | 2/2002 |

\* cited by examiner

*Primary Examiner*—Nicholas D Lucchesi
*Assistant Examiner*—Scott Medway
(74) *Attorney, Agent, or Firm*—Sughrue Mion, PLLC (57) ABSTRACT

Parts of a powdered medicine multi-dose administering device are assembled, powdered medicine is filled and assembly that is obtained is inspected all on an automatic production line to increase productivity while preventing the production of defective products. The powdered medicine multi-dose administering device is produced through automated steps of inserting a filter (12) in a filter-fitting portion (11*a*) of a container (10), inserting an inner cylinder (15) in the container body (10), filling the container with the powdered medicine through a ring-like opening between an opening in the upper part of the container and the inner cylinder, fitting an inner closure (19) to the container and to the inner cylinder, fitting a nozzle (20) to the container while coupling it to the inner cylinder, and inspecting the thus obtained assembly.

32 Claims, 8 Drawing Sheets

METHOD OF PRODUCING POWERED MEDICINE MULTI-DOSE ADMINISTERING DEVICE AND APPARATUS THEREOF

TECHNICAL FIELD

The present invention relates to an apparatus and a method of producing powered medicine multi-dose administering devices and, particularly, to a method and apparatus for producing powdered medicine multi-dose administering devices which are capable of administering the powdered medicine any number of times.

A powdered medicine multi-dose (many times) administering device contains a medicine, in an amount for a plurality of times of administration, in a container and measures and administers the medicine in an amount for a single administration each time. In producing and assembling the administering devices of this kind, the steps are automatically carried out for assembling the parts and for filling the devices with the powdered medicine of a predetermined amount enough for a plurality of times of administration, and the devices, after being assembled, are all inspected. Thus, there are provided a method and an apparatus for automatically producing the powdered medicine multi-dose administering devices guaranteeing a high degree of quality.

BACKGROUND ART

The powdered medicine multi-dose administering devices have heretofore been produced by assembling individual parts and filling the devices with the powdered medicine separately from each other. Therefore, the assembling operation and the operation for filling the medicine have not been automatically carried out and, hence, cumbersome operations must be carried out through many steps.

A prior art has been taught in Japanese Examined Patent Publication (Kokoku) No. 5-48710 which is related to a dispenser for inhaling an aromatic substance, a method of producing the dispenser, and a production line therefor including a production step of automatically filling microcapsules in a chamber defined between a flat dish and a closure.

However, the manual work for assembling the powdered medicine multi-dosage administering devices of the above prior art is not only low productively but also permits the defective products to be assembled due to mistakes at a rate of several percent. Besides, performance inspection by human hand is so slow that it is impossible to inspect all of the products thus, inviting a problem in that defective products may occur in the products.

DISCLOSURE OF THE INVENTION

It is therefore an object of the present invention to provide a method and an apparatus for automatically assembling the parts of a powdered medicine multi-dose administering device, for automatically filling the powdered medicine, and for automatically conducting the inspection after assembly.

In order to achieve the above object according to the present invention, there is provided a method of producing a powdered medicine multi-dose administering device which includes a container capable of storing a multi-dose amount of powdered medicine and having, in the bottom portion thereof, a hole for containing a single-dose amount of the medicine and filter-fitting portions, a filter fitted into the filter-fitting portion, an inner cylinder capable of being rotated between a filling position and an administering position while maintaining contact with the inner bottom surface of the container, an inner closure having a center hole for rotatably supporting an upper part of the inner cylinder and for closing an opening at the upper end of the container being fitted to the inner periphery of the opening at the upper part of the container, and a nozzle coupled to the upper end of the inner cylinder, so as to transmit the rotation, rotatably fitted to the outer periphery of the opening at the upper part of the container and having a medicine blow-out passage, wherein, at the filling position, the powdered medicine in the container is supplied to the medicine-containing hole through an opening in the inner cylinder, and, at the administering position, the air is blown into the medicine-containing hole through the filter, so that the medicine in the medicine-containing hole is blown out to the exterior through the medicine passage of the inner cylinder and the medicine blow-out passage of the nozzle, said method of producing a powdered medicine multi-dose administering device comprising the steps of:

inserting the filter in the filter-fitting portion;
inserting the inner cylinder in the container body;
filling the container with the powdered medicine;
fitting the inner closure to the container and to the inner cylinder; and
fitting the nozzle to the container while coupling it to the inner cylinder.

In the bottom of the container, there are provided a second hole and a second filter-fitting portion in addition to the medicine-containing hole (first hole) and the filter (first filter)-fitting portion, a second filter coarser than the first filter is fitted to the second filter-fitting portion, and the second filter and the second hole are communicated with the medicine passage in the inner cylinder at the time of filling the powdered medicine. Here, the method includes a step of inserting the second filter in the second filter-fitting portion prior to inserting the first filter in the first filter-fitting portion.

In the step of inserting the first and second filters, the container is installed with its bottom portion faced upward. Then, the first and second filters can be inserted in the container, downward, from the upper side.

In the step of inserting the first and second filters, the insertion is conducted while applying insertion guides to the first and second filter-fitting portions, respectively. This enables the filters to be smoothly inserted even when there is almost no clearance between the filters and the filter-fitting portions.

At the time of inserting the first filter in the first filter-fitting portion, the up-and-down direction of the filter is confirmed while, at the time of inserting the second filter in the second filter-fitting portion, the up-and-down direction of the filter is not confirmed. The first filter has a protruded or recessed shape on the side of the powdered medicine-containing hole to adjust the volume of the medicine-containing hole thereby to finely adjust the single-dose amount. Therefore, the first filter is inserted after the up-and-down direction thereof is confirmed.

In inserting the first filter in the first filter-fitting portion, the first filter is false-inserted in a first step and is, then, press-inserted in a next step.

After the second filter is inserted in the second filter-fitting portion, the depth of insertion of the second filter is measured and after the first filter is press-inserted in the first filter-fitting portion, the depth of press-insertion of the first filter is measured.

After the first and second filters have been inserted in the first and second filter-fitting portions, the container is turned upside down. In the subsequent steps, therefore, the operation can be carried out with the side of the opening of the container faced upward.

The step of inserting the first and second filters is executed while the container is being conveyed by a first conveyer, and the step after the container is turned upside down is executed while the container is being conveyed by a second conveyer.

In transferring the container onto the first conveyer, the position of the container in the rotational direction is determined by utilizing a protrusion provided at a central portion on the inner bottom surface of the container. In transferring the container body onto the second conveyer, the position of the container in the rotational direction is determined by utilizing the first and second filter-fitting portions that are protruding outward from the bottom portion of the container body.

After the container is transferred onto the second conveyer, the interior of the container is cleaned by injecting compressed air into the container and sucking the air prior to inserting the inner cylinder in the container.

In inserting the inner cylinder in the container, the position of the inner cylinder in the rotational direction is determined by utilizing a non-circular portion (one of the concrete examples may be a pentagonal shape which is not an ortho-pentagonal shape, such as a "home-base" shape) formed at a portion coupled to the nozzle at the upper end of the inner cylinder.

After the inner cylinder is inserted in the container, the depth of insertion of the inner cylinder is measured. Further, after the inner cylinder is inserted in the container, the container is cleaned again by supplying air therein while holding the interior of the container body by the inner cylinder.

In the step of filling the container with the powdered medicine, the container is filled with the powdered medicine through a ring-like opening between the opening at the upper end of the container and the inner cylinder by utilizing a funnel for filling.

In the step of filling the container with the powdered medicine, the container is vibrated. Then, a medicine storage chamber defined in the container is densely filled with the powdered medicine.

In the step of inserting the inner closure in the container, the inner closure is secured and fitted to the inner periphery of the opening at the upper part of the container and, at the same time, the rotary shaft portion at the upper part of the inner cylinder is fitted to the center hole of the inner closure in a non-fixed manner. Then, the inner closure is secured to the container to close the opening at the upper end of the container while rotatably supporting the inner cylinder.

In the step of inserting the inner closure in the container, the inner closure is false-inserted in the container in a first step and is, then, press-inserted in the container in a next step.

In press-inserting the inner closure in the container, the inner closure is press-inserted in the container while holding the upper end of the inner cylinder that is protruded upward beyond the inner closure.

In holding the upper end of the inner cylinder, the position of the inner cylinder is corrected at the same time. After the inner closure is fitted into the container and the inner cylinder, the depth of insertion of the inner closure is measured.

In the step of inserting the nozzle in the container, the nozzle is fitted in a non-fixed manner to the outer periphery of the opening at the upper part of the container body and, at the same time, a non-circular hole of the nozzle is coupled to the upper end of the inner cylinder in a manner to transmit rotation. Then, the nozzle is supported so as to rotate relative to the container. By turning the nozzle, further, the inner cylinder, too, rotates in the container at the same time.

In the step of inserting the nozzle in the container, a pin is inserted in the noncircular hole of the nozzle that corresponds to the noncircular portion at the upper end of the inner cylinder prior to inserting the nozzle, thereby to determine the position of the nozzle in the direction of rotation. After the nozzle is inserted in the container, the depth of insertion of the nozzle is measured.

The invention further provides a method of assembling a powdered medicine administering device which permits an inner cylinder to move between a medicine filling position and a blow-out position upon turning a nozzle, comprising the steps of:

incorporating a filter on the outer side of a bottom portion of a container with the bottom portion being positioned on the upper side;

turning the container upside down so that the open end of the container faces upward;

inserting the inner cylinder in the container from the side of open end of the container;

filling the container with a predetermined amount of powdered medicine from the side of open end of the container;

securing and fitting the inner closure to the open end of the container as well as to the inner cylinder so that the inner cylinder partly protrudes toward outside of the container; and rotatably fitting the nozzle to the open end of the container while coupling it to the inner closure in a manner to transmit the rotation.

The present invention further provides a method of producing a powdered medicine multi-dose administering device, comprising the steps of:

inserting the filters in the filter-fitting portions;

inserting an inner cylinder in a container body;

filling the container with the powdered medicine;

fitting the inner closure to the container and to the inner cylinder;

fitting a nozzle to the container while coupling it to the inner cylinder; and inspecting the thus obtained assembly.

In a step where the assembly is obtained, the inner cylinder is set at the administering position, and the step of inspecting the assembly comprises the steps of:

measuring the initial load of the assembly;

turning the nozzle by a predetermined angle relative to the container body to bring the inner cylinder to the filling position;

vibrating the assembly;

turning the nozzle in the opposite direction by a predetermined angle relative to the container body to bring the inner cylinder to the administering position;

sucking air from the end of the nozzle while injecting compressed air through the filter so that a single-dose amount of the powdered medicine in the medicine-containing hole is injected from the nozzle; and measuring the load of the assembly after the injection and calculating the amount of injection from the weight difference of before and after the injection.

After the initial load of the assembly is measured, the assembly is transferred onto the index table, and the individual steps in the step of inspection are executed while the index table is being turned.

A rotary cylinder is used in the above two steps of turning the nozzle relative to the container body, and an urethane rubber is arranged at the chuck portion of the rotary cylinder that comes in contact with the nozzle. This prevents the chuck from coming into local contact, and the rubber is not abraded.

The invention further provides an apparatus for automatically producing a powdered medicine multi-dose administering device, comprising:

a production line for inserting the filters in the filter-fitting portions, inserting the inner cylinder in the container body, filling the container with the powdered medicine, fitting the inner closure to the container and to the inner cylinder, and fitting the nozzle to the container while coupling it to the inner cylinder to produce an assembly; and an inspection line for inspecting the assembly that is produced and for measuring the amount of injection of a single-dose amount of the powdered medicine.

BEST MODE FOR CARRYING OUT THE INVENTION

Figure 7:
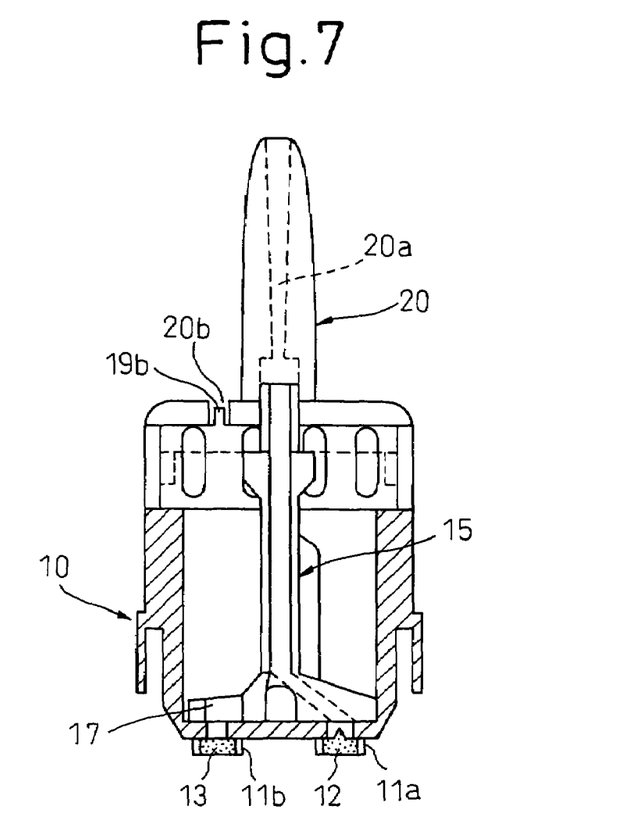
FIG. 7 is a view illustrating an assembly of a powdered medicine multi-dose administering device that is completed.
Figure 8:
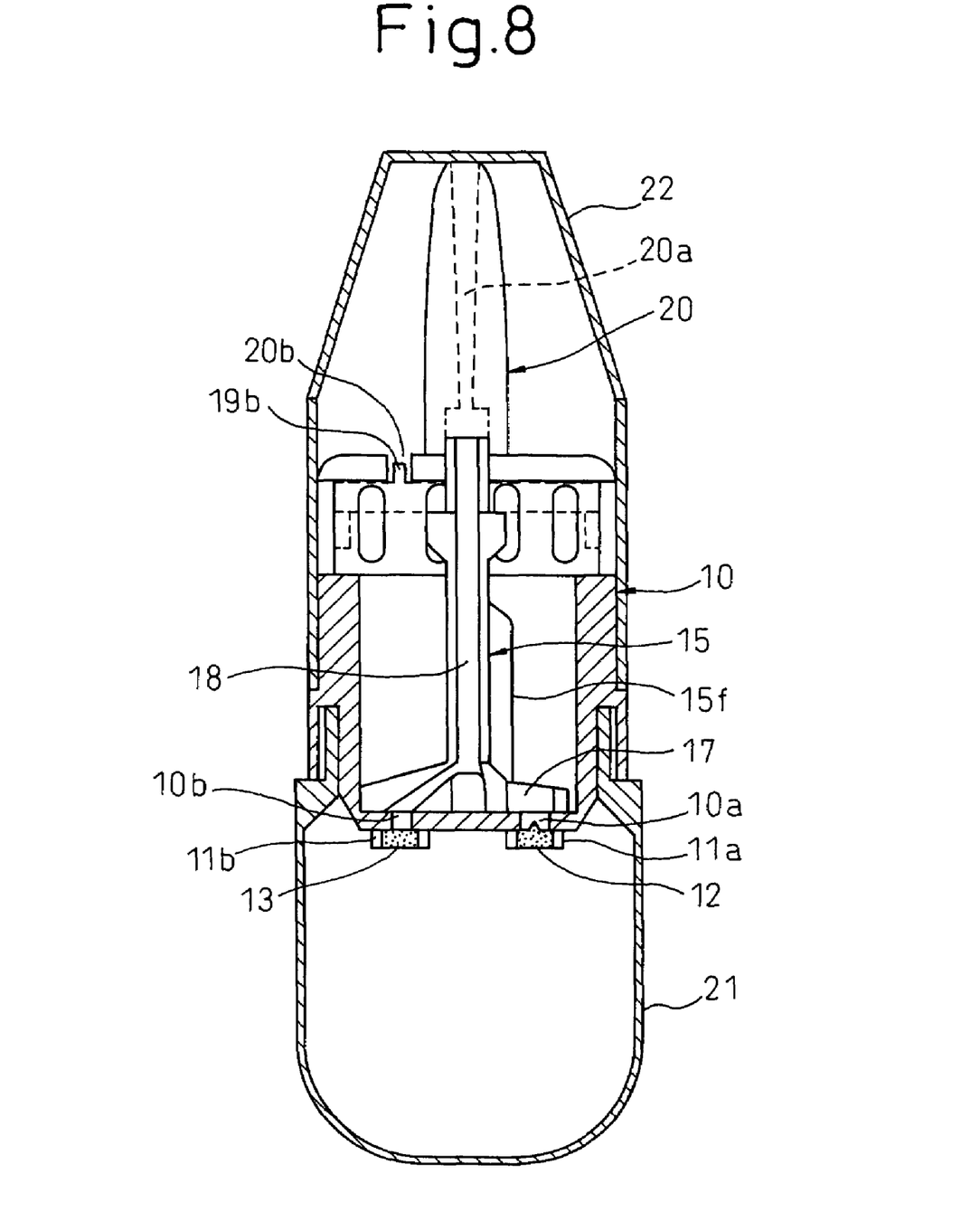
FIG. 8 is a view illustrating the powdered medicine multi-dose administering device that is completed.
Figure 9:
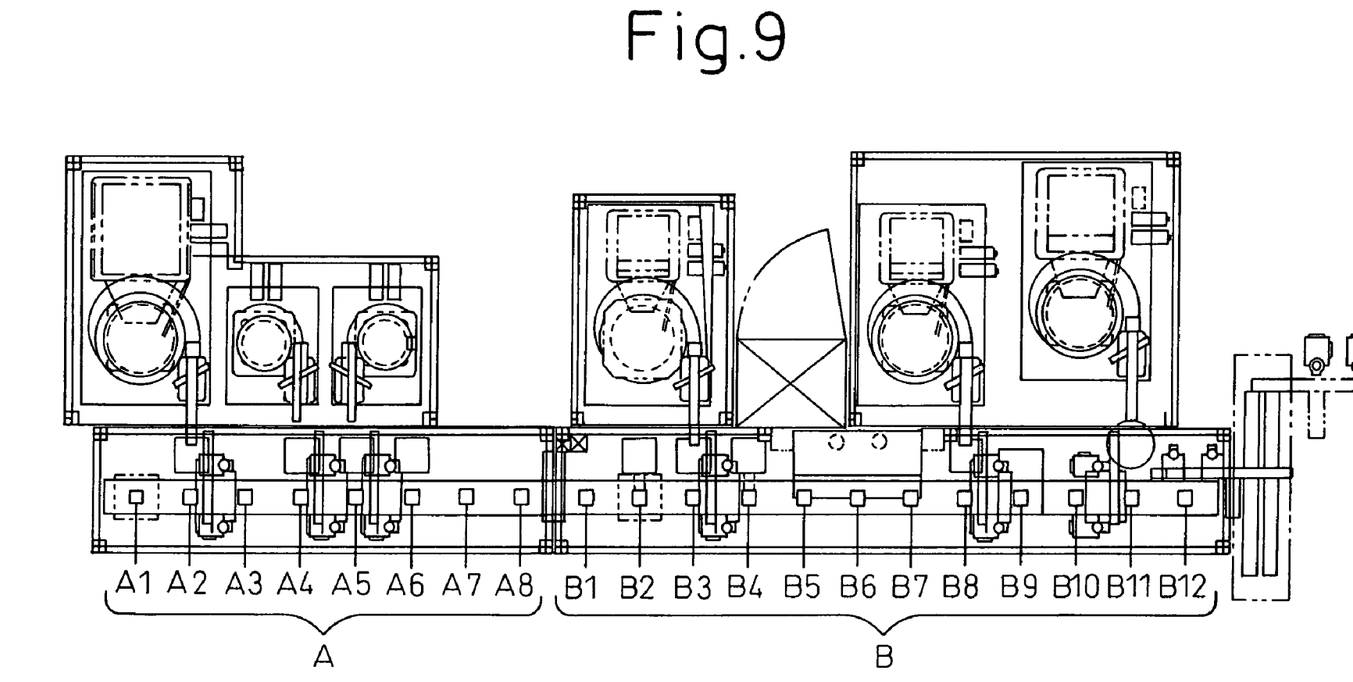
FIG. 9 is a view of a production line for producing the assembly of the powdered medicine multi-dose administering device.

An embodiment of the invention will now be described in detail with reference to the accompanying drawings. First, briefly described below with reference to FIGS. 1 to 9 are the steps of producing a powdered medicine multi-dose (many times) administering device of the present invention. FIG. 7 is a view illustrating an assembly of the powdered medicine multi-dose administering device that is completed, FIG. 8 is a view illustrating the administering device that is completed, and to which a pump and a cap are attached, and FIG. 9 is a view illustrating an apparatus for production.

Figure 1:
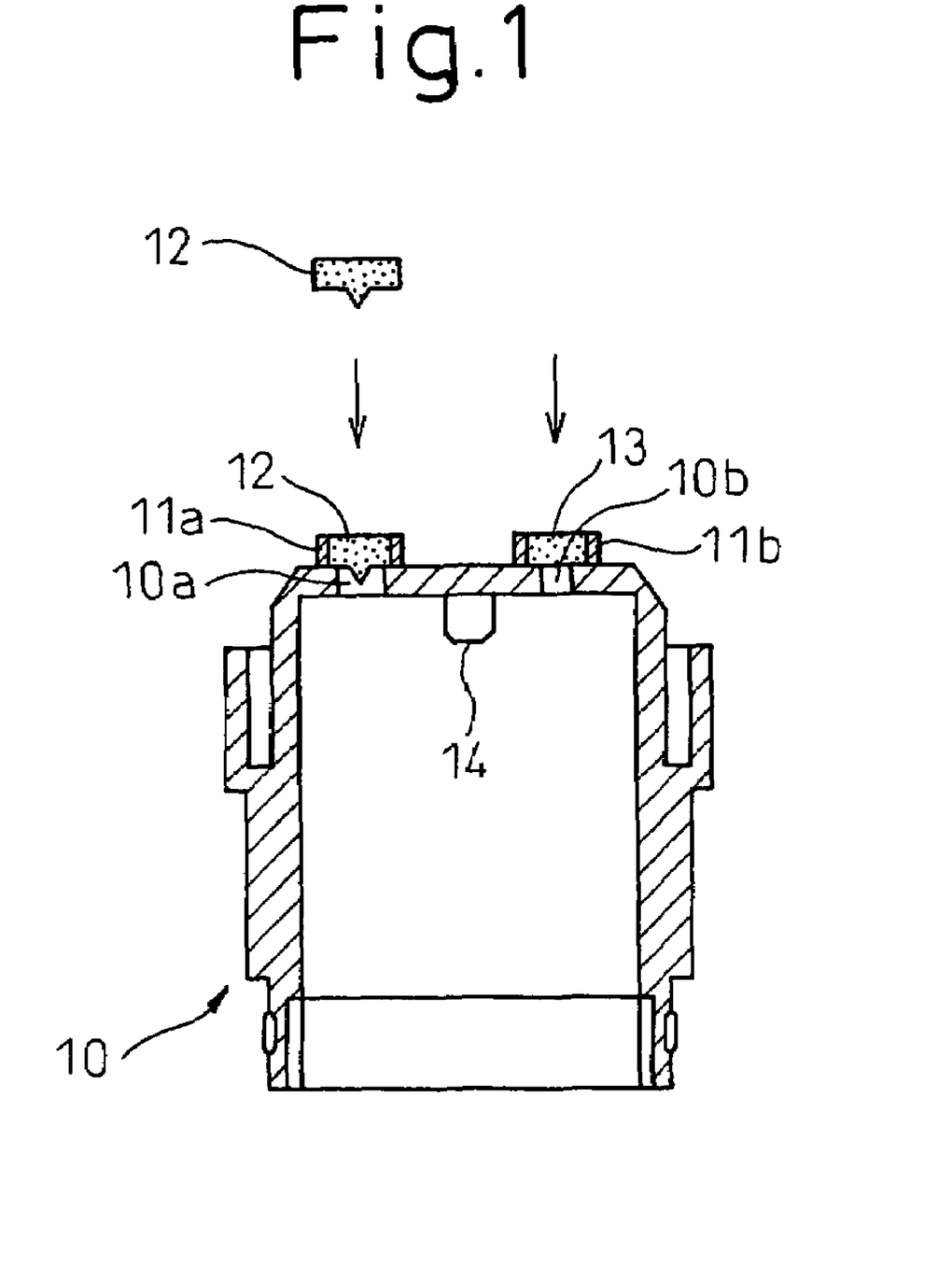
FIG. 1 is a view illustrating a step of inserting filters.

FIG. 1 illustrates a step of inserting two filters in the container body. The container body 10 is made of a suitable resin in nearly a cylindrical shape with its one end open and having a closed bottom portion at the other end. The container 10 contains a powdered medicine in a predetermined amount enough for a plurality of times of administration. In the first step prior to filling the powdered medicine, two filters 12 and 13 are inserted in the bottom portion. In this step, the container 10 is turned upside down so that the filters can be easily and reliably inserted; i.e., the container 10 is placed with its bottom portion facing upward.

Two holes 10a and 10b are formed in the bottom wall of the container 10. These holes 10a and 10b are formed at positions of an equal distance from the center line of the container in the radial direction, and are maintaining a predetermined angle relative to the center line. This angle corresponds to a rotational angle α (FIG. 6) along which the inner cylinder 15 turns between the filling position and the administering position that will be described later. Ring-like filter-fitting portions 11a and 11b are provided on the container on the outer sides of the holes 10a and 10b so that the filters 12 and 13 can be fitted thereto. One hole 10a has a size corresponding to a single-dose amount of the powdered medicine, and specifies the medicine-containing hole. Here, the capacity of the medicine-containing hole 10a can be finely adjusted depending upon the shape of the filter 12.

A protrusion 14 is formed on the inside of the bottom of the container 10 along the center line. In the step of inserting the filters 12 and 13, the position of the container 10 in the rotational direction is determined by utilizing the protrusion 14.

The filter 12 corresponding to the medicine-containing hole 10a is a dense filter, and has a protruded or recessed portion for finely adjusting the capacity of the hole 10a. In FIG. 1, the dense filter 12, as illustrated, possesses a protrusion. Depending upon the case, however, the dense filter 12 may have a recess. Therefore, the filter must be inserted in the fitting portion 11a while defining the up-and-down insertion direction such that the protrusion or the recess faces the side of the measuring hole 10a. The filter 13 fitted to the other hole 10b which is the air hole is a coarse filter. The volume of the hole 10b need not be adjusted. Therefore, the limitation of up-and-down direction is not imposed on the filter 13 that is inserted in the fitting portion 11b.

In the step of inserting the filters, the coarse filter 13 is inserted, first, in the fitting portion 11b. Then, the dense filter 12 is inserted in the fitting portion 11a. The up-and-down direction of the dense filter 12 is checked by using a sensor such as a micro-gauge. When the up-and-down direction of the dense filter 12 is reversed, this filter is not used, or this filter is used upon turning the same in the up-and-down direction (inverting the concave/convex direction).

The filters 12 and 13 to be inserted are of a column shape. However, as there is almost no clearance relative to the fitting portions 11a and 11b, a guide (not shown) is used at the time of insertion. Further, the depth of insertion of the filter is checked by using a cylinder sensor and a photo sensor.

In the production apparatus illustrated in FIG. 9, the step of inserting the filters of FIG. 1 is conducted on a conveyer A. The conveyer A moves the workpiece linearly and intermittently, so that the processings are executed at stations A1 to A8.

A stage A1 is idle and, at a stage A2, the container 10 is transferred onto the conveyer A by utilizing the XY-axis cylinder. The position of the container 10 that is transferred is detected by a cylinder sensor and a photo sensor. Next, a stage A3 is idle, and the coarse filter 13 is inserted at a stage A4. At a stage A5, the dense filter 12 is provisionally inserted and, at a stage A6, the dense filter 12 is tightly press-inserted and the depth of insertion is detected by a cylinder sensor and a photo sensor. At a stage A7, the depth of insertion of the dense filter 12 is confirmed by a digital gauge, and the presence of the coarse filter 13 is also detected. At a stage A8, the workpiece of container is transferred onto a second conveyer B.

At the time of transfer, the workpiece (container 10) is turned upside down. Like the first conveyer A, the second conveyer B, too, moves the workpiece linearly and intermittently, so that the processings are executed at stations B1 to B12. At a stage B1, the work (container) is transferred onto the second conveyer B and, at a stage B2, air is injected and simultaneously sucked to clean the interior of the container 10.

Figure 2:
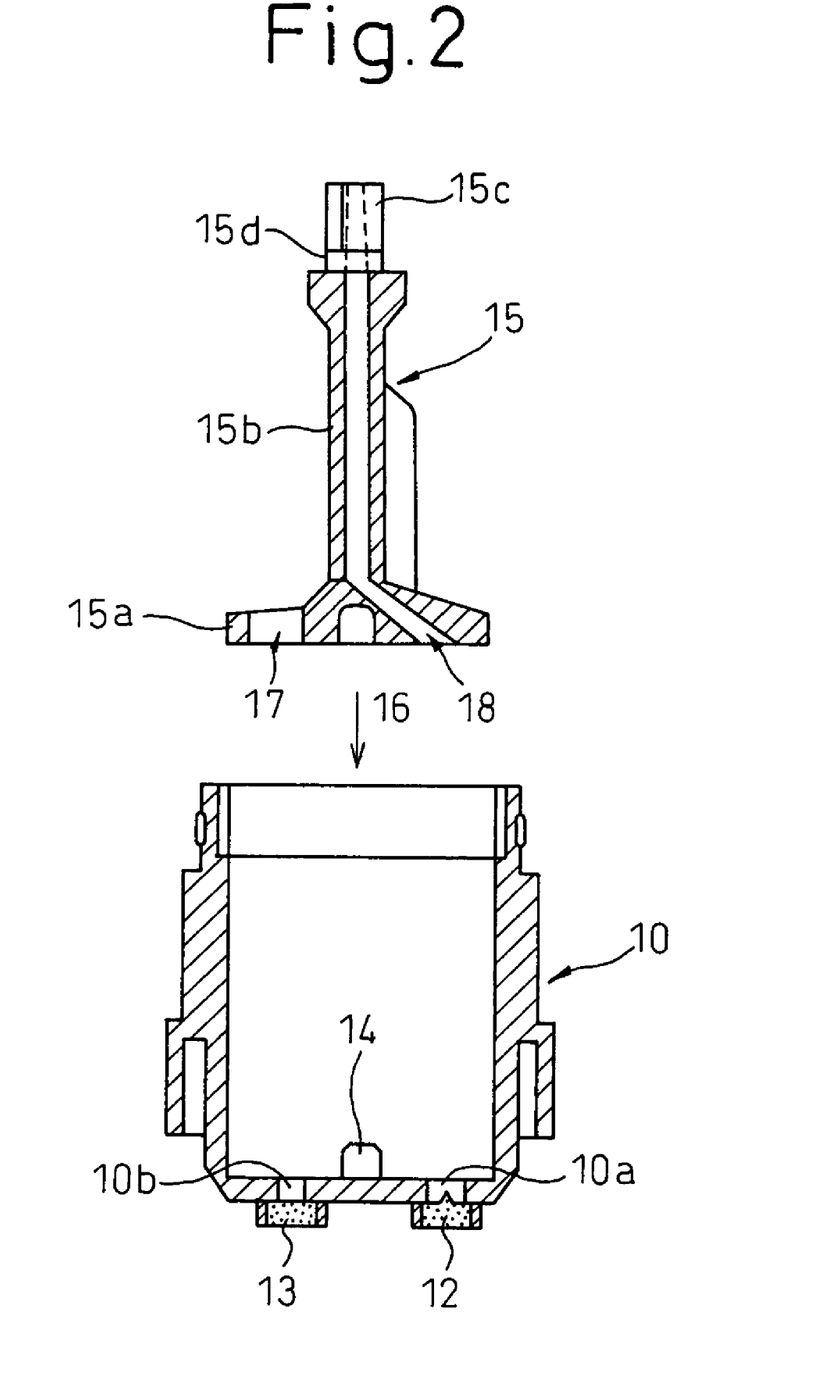
FIG. 2 is a view illustrating a step of inserting an inner cylinder.

FIG. 2 illustrates a step (stage B3) of inserting the inner cylinder in the body. The inner cylinder 15 for introducing the powdered medicine is integrally constituted, of resin, of a bottom portion 15a having a diameter nearly same as or slightly smaller than the inner bottom wall surface of the container 10, and a cylindrical portion 15b having a medicine introduction passage 18 extending therein in the up-and-down direction. The cylindrical portion 15b has, at its upper portion, a sectional portion 15c of a noncircular shape (e.g., a home base-like pentagonal shape of which the two neighboring angles become 90 degrees) for transmitting the rotation, and a rotary shaft portion 15d. At the center of the bottom portion 15a, there is formed a hole 16 that rotatably fits to the central protrusion 14 of the container 10. With the hole 16 as a center, a through opening 17 is formed on one side and, on the other side, a medicine introduction passage 18 is opened at the bottom surface.

Figure 6:
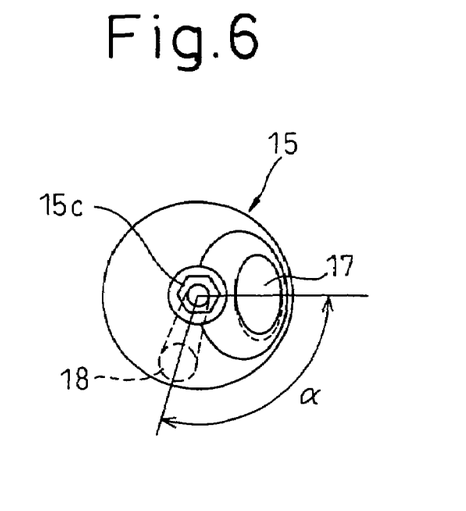
FIG. 6 is a plan view of the inner cylinder.

The opening 17 is penetrating through the bottom portion 15a, in the up-and-down direction, and it assumes a shape that is widened upward as shown in FIG. 6 to enable the medicine-containing hole 10a to be easily filled with the powdered medicine contained in the container 10. On the other hand, the medicine introduction passage 18 has its lower end opened in the lower surface of the bottom portion 15a, and extends upward and in an inclined manner from this opening portion up to the center axis of the cylindrical portion 15b and, further, extends upward along the center axis and is opened at the upper end of the noncircular portion 15c.

On inserting the inner cylinder 15 in the container body 10, the position of the inner cylinder 15 in the rotational direction is determined by utilizing the noncircular portion 15c at the upper end thereof. The depth of insertion of the inner cylinder 15 in the container body 10 is checked by the cylinder sensor and the photo sensor.

After the inner cylinder 15 is inserted, the interior of the container body 10 is cleaned with the air at a stage B4 while being held by the inner cylinder 15. A stage B5 is idle, and the powdered medicine is filled at a stage B6.

Figure 3:
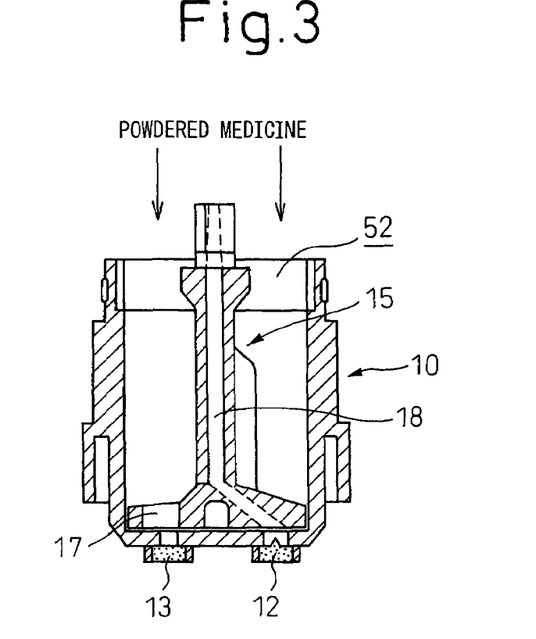
FIG. 3 is a view illustrating a step of filling a powdered medicine.
Figure 10:
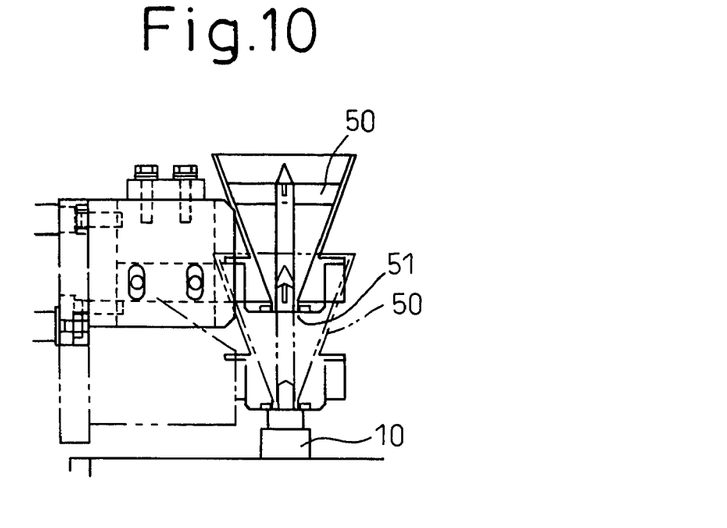
FIG. 10 is a view illustrating a mechanism for filling the powdered medicine.

FIG. 3 illustrates a step (stage B6) for filling the container body with the powdered medicine of a predetermined amount for a plurality of times of administration. The powdered medicine must be filled through a ring-like opening 52 between the container 10 and the inner cylinder 15 and, hence, a filling funnel 50 is used as shown in FIG. 10. The filling funnel 50 has a ring-like medicine outlet 51 corresponding to the ring-like opening 52 of the workpiece (container body) 10. In order to fill the powdered medicine as densely as possible, further, the container 10 is vibrated. The filling funnel 50 has a double structure to prevent the positional deviation of the inner cylinder 15 due to vibration, to prevent dispersion, and to prevent the adhesion of the powdered medicine on the inner cylinder 15 at the time of filling. In order to prevent the adhesion of powder on the outer walls of the container body 10 at the time of filling and to clean the outlet of the filling funnel 50 right after the filling, further, a shutter is used to close the ring-like medicine outlet 51 thereby to collect the dust from local area. In FIG. 10, the solid line represents a state where the filling funnel 50 is retreated upward and a broken line represents a filling state where the filling funnel 50 is lowered down to a position where it comes in contact with the container 10.

Figure 4:
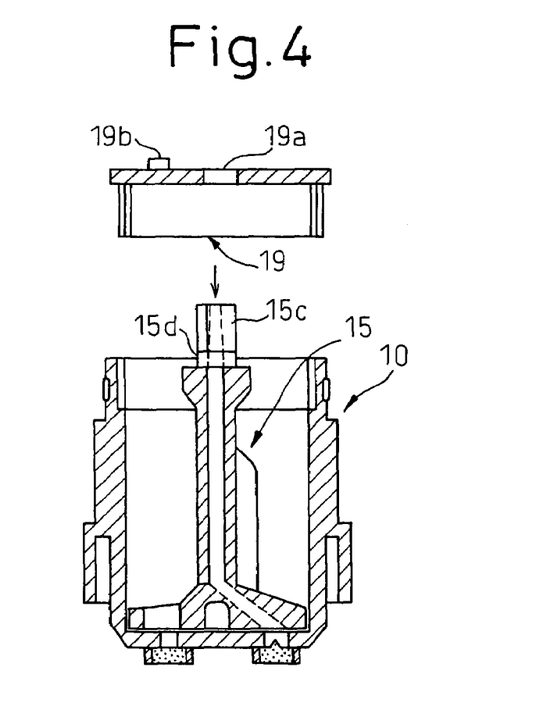
FIG. 4 is a view illustrating a step of inserting an inner closure.

FIG. 4 illustrates a step for inserting the inner closure in the container body. The inner closure 19 is integrally molded by using a resin, and includes a nearly circular closure portion for the container 10 and a cylindrical portion that fits to the upper inner wall surface of the container 10. At a central position of the closure portion, there is formed a hole 19a to which will be rotatably fitted a portion of the rotary shaft 15d of the inner cylinder 15. Further, a protrusion 19b is provided at a position spaced away from the center hole 19a in the radial direction to protrude outward beyond the closure portion so as to be fitted to a arch-shaped slit 20b (FIG. 5) for limiting the angle of rotation of the nozzle 20 that will be described later.

The inner closure 19 is inserted in two stages. Namely, in the production apparatus of FIG. 9, a stage B7 is idle, and a stage B8 is for provisionally inserting the inner closure 19 (first stage). In the first stage, the inner closure 19 is provisionally inserted by utilizing the XY-axis cylinder. The inner closure 19 is positioned in the rotational direction by chucking the protrusion 19b of the inner closure 19 that is air-adsorbed. To prevent the positional deviation and movement of the inner cylinder 15 when the inner closure 19 is inserted, the inner cylinder 15 is inserted in a fixed manner while holding the upper end of the noncircular portion 15c of the inner cylinder 15. The depth of insertion is checked by using the cylinder sensor and the photo sensor. The holder portion of the inner cylinder 15, i.e., the pentagonal portion at the upper end is of a tapered structure, and the inner cylinder 15 is corrected for its position simultaneously when it is being inserted.

At a second stage (stage B9) of inserting the inner closure 19, the inner closure 19 is press-inserted in the container 10 by utilizing a short-axis cylinder. As in the first stage, the inner cylinder 15 is inserted while being held to prevent the positional deviation and shakiness of the inner cylinder 15. The depth of insertion is checked by the cylinder sensor and the photo sensor. The position of the inner cylinder 15 is also corrected at the same time by utilizing the holder portion of the inner cylinder 15.

Figure 5:
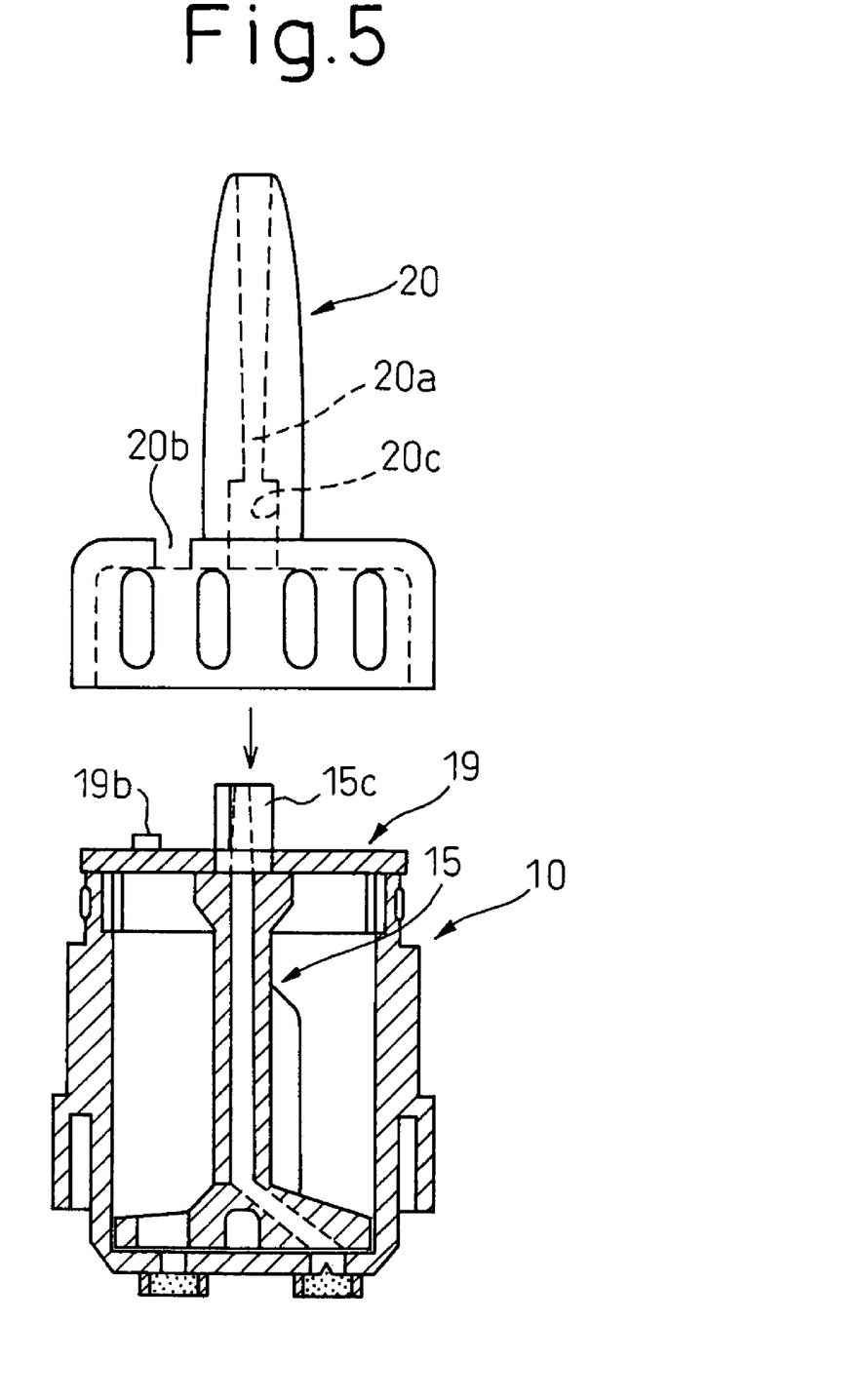
FIG. 5 is a view of inserting a nozzle.

FIG. 5 is a view illustrating a step for inserting the nozzle. In the production apparatus of FIG. 9, a stage B10 is idle and a stage B11 is for inserting the nozzle. The nozzle 20 is integrally constituted of a resin and includes a portion forming a passage 20a for the powdered medicine and a cylindrical portion which rotatably fits to the upper peripheral surface of the container 10, and has a arch-shaped slit 20b that fits to the protrusion 19b of the inner closure 19. Further, the nozzle 20 has a noncircular hole 20c that fits to the noncircular portion 15c at the upper end of the inner cylinder 15. This transmits the rotation of the nozzle 20 to the inner cylinder 15.

The nozzle 20 is inserted by utilizing the XY-axis cylinder. The nozzle 20 is positioned in the rotational direction by inserting a noncircular pin (not shown) in the noncircular hole 20c of the nozzle 20 that is air-adsorbed. The depth of insertion of the nozzle 20 in the container 10 is checked by the cylinder sensor and the photo sensor.

Thus, an assembled product of the powdered medicine multi-dose administering device is completed as shown in FIG. 7, and is transferred to an inspection machine at the next step from the second conveyer B in the stage B12 of FIG. 9. When it is found that a defective product is produced as a result of inspection through the above steps, the product is discharged prior to being transferred to the inspection machine.

Figure 11:
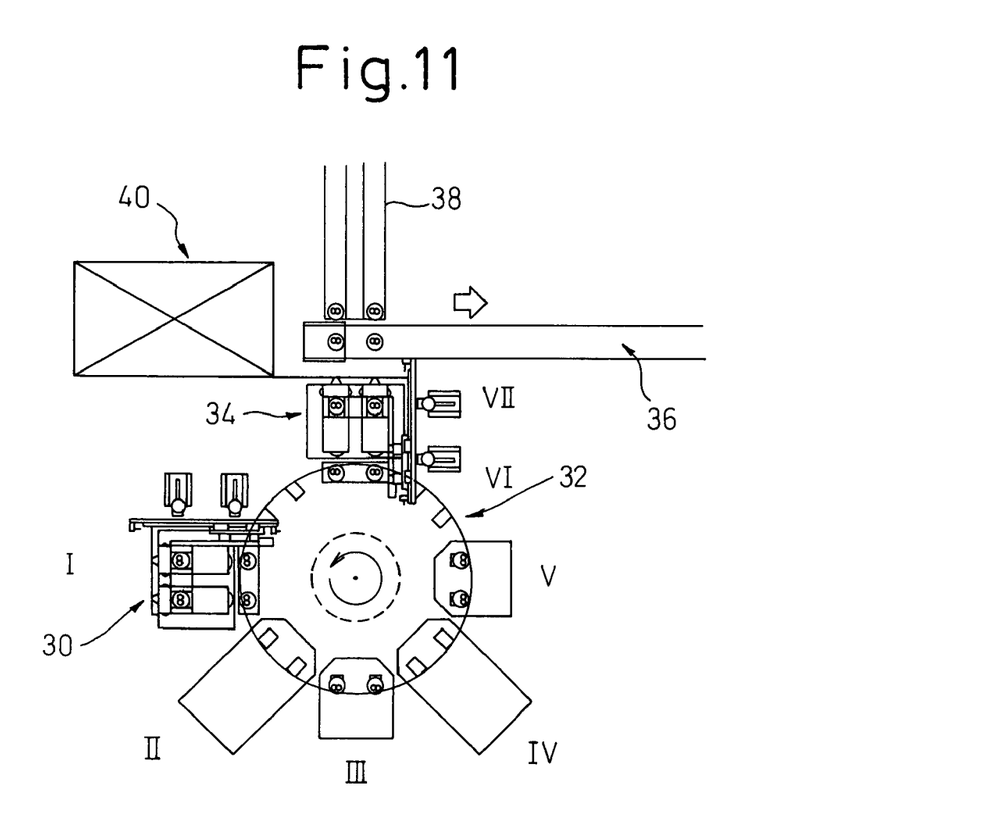
FIG. 11 is a view illustrating a device for inspecting the assembly of the powdered medicine multi-dose administering device.

FIG. 11 is a view illustrating a step of inspecting the assembly filled with the medicine.

The assemblies are, first, placed in pairs on an electronic balance 30 by utilizing the XY-axis cylinder. The electronic balance 30 is provided with a windbreak.

After the measurement, the assembled products are placed in pairs on a rotary index table 32 (first stage) by utilizing the XY-axis cylinder. On the index table 32, pairs of assembled products are successively sent to the first to seventh stages (I to VII) where they are inspection processed. In the first stage, the assembled products are positioned in the rotational direction by utilizing the protrusion of the filter-fitting portion.

Then, at a second stage, the nozzle 20 is turned counterclockwise by a predetermined angle by utilizing the rotary cylinder. In this case, the rotational torque is measured by using a load cell. The chuck portions that come in contact with the nozzle are made of a tubular urethane rubber of a circular shape that are arranged maintaining a predetermined distance to prevent the local contact with the product and to suppress the wear of the rubber. In a state after assembled but before being inspected, the nozzle 20 and the inner cylinder 15 of the assembly are at the administering position, and the medicine-containing hole 12 is not communicated with the opening 17. Therefore, the medicine has not been filled. Upon being turned counterclockwise in the second stage, however, the nozzle 20 and the inner cylinder 15 are at the filling position where the opening 17 of the inner cylinder 15 is communicated with the medicine-containing hole 10a, and the medicine-containing hole 10 is filled with the powdered medicine in the container 10 due to its own weight.

Next, at a third stage, the product is vibrated up and down (by tapping) by a roller cam driven by a servo motor. This enables the medicine-containing hole 10a to be reliably filled with the powdered medicine of a predetermined amount. To prevent the assembled product from bouncing due to the shock at the time of tapping, shock absorbers are placed on and under the vibrating portion.

Next, at a fourth stage, the nozzle 20 is turned clockwise by utilizing the rotary cylinder. Here, the rotational torque is measured by using the load cell. In this case, too, the chuck portions that come in contact with the nozzle are made of a tubular urethane rubber of a circular shape that are arranged maintaining a predetermined distance to prevent the local contact with the product and to suppress the wear of rubber. Due to the rotation, the nozzle 20 and the inner cylinder 15 of the assembly are at the administering positions, and the medicine-containing hole 10a is in a state of being communicated with the medicine passages 18 and 20a.

Then, at a fifth stage, the air is sucked from the end of the nozzle 20 and, at the same time, the compressed air is injected, as a pulse, through the filter 12 to spray the powdered medicine. This state of spraying is inspected as being the practically established state using the pump 21 (FIG. 8) of the powdered medicine multi-dose administering device.

A sixth stage is idle and, at the seventh and last stage, the assembled products are placed on the electronic balance 34 by utilizing the XY-axis cylinder, and the weight is measured after the spraying. The electronic balance 34 is installed on a vibration-proof plate and is provided with a windbreak.

After the measurement, the assembled products are placed on the index table by utilizing the XY-axis cylinder. The amount sprayed is calculated from the difference of weights before and after the spraying. The measured results are displayed on the control board/display unit 40. As a result of inspection, the acceptable products of which the one time of spraying amount is within a predetermined range (e.g., 15 mg±1.5 mg) are discharged to a takeout port through an acceptable product discharge chute 36 and the assembled products that are determined to be defective are discharged through a defective product discharge chute 38.

Upon mounting the pump 21 and the cap 22 on the assembled product filled with the medicine shown in FIG. 7, a powdered medicine multi-dose (many times) administering device is completed as shown in FIG. 8.

Next, briefly described below is how to use the thus completed powdered medicine multi-dose administering device.

To use the device as shown in FIG. 8, the cap 22 is removed. Usually, the device is in the state of after an administration and the inner cylinder 15 is at the administering position. Therefore, the medicine-containing hole 10a in the bottom surface of the container 10 is opened to the medicine passage 18 in the inner cylinder 15 and is communicated with the exterior.

In this state, the nozzle 20 is turned counterclockwise by a predetermined angle. This rotational angle is limited because the protrusion 19b of the inner closure 19 has been engaged with the arch-shaped slit 20b of the nozzle 20. As the nozzle 20 is turned counterclockwise by a predetermined angle, the inner cylinder 15 coupled to the nozzle 20 so as to transmit the rotation and is turned counterclockwise by the same angle α as that of the nozzle 20 as shown in FIG. 6. Blades 15f work to stir the powdered medicine in the container as the inner cylinder 15 is turned, and the amount of medicine does not deviate.

The opening 17 in the inner cylinder 15 is positioned on the medicine-containing hole 11a which, therefore, is filled with the powdered medicine in the container 10, due to its own weight, through the opening 17. The single-dose amount of the powdered medicine is adjusted by the protrusion or recess of the filter 12 as described earlier. In filling the medicine, the interior of the pump 21 is communicated with the exterior through the filter 13, hole 10b and passages 18, 20a. At the time of filling the medicine-containing hole 10a with the powdered medicine through the opening 17, therefore, the air escapes therethrough, and the medicine is smoothly filled.

Next, the nozzle 20 is returned clockwise by the predetermined angle α. The inner cylinder 15, too, is turned clockwise by the same angle α. In the early stage of rotation, the medicine-containing hole 10a is once swept by the bottom surface of the inner cylinder 15 to measure the single-dose amount of the powdered medicine. When turned by the predetermined angle, the administering position is reached where the medicine passage 18 of the inner cylinder 15 is brought to a position where it is communicated with the medicine-containing hole 10a.

In this state, the pump 21 is depressed to blow the air into the powdered medicine-containing hole 10a through the filter 12, whereby the powdered medicine is injected to the exterior through the medicine passage 18 in the inner cylinder and through the medicine injection passage 20a of the nozzle 20, and the powdered medicine is applied to a diseased part. At the administering position, the hole 10b is closed by the lower surface of the inner cylinder 15. Therefore, the pressure produced by the pump 21 is effectively used for blowing out the medicine.

Though the embodiment of the invention was described above with reference to the accompanying drawings, it should be noted that the invention is in no way limited to the above embodiment only but can be realized in a variety of forms or can be modified or changed without departing from the spirit and scope of the invention.

INDUSTRIAL APPLICABILITY

According to the present invention as described above, there are provided an apparatus and a method of automatically assembling the parts of the powdered medicine multi-dose administering device, automatically filling the powdered medicine and of automatically conducting the inspection after the assembly. That is, through the steps of production and assembly, the workpieces are transferred onto a known straight-forward conveyer and a rotary index table, and the individual parts are assembled on a completely automated line that includes an XY-axis cylinder and a rotary cylinder. The production efficiency is greatly enhanced. Further, mistakes are prevented owing to correct inspection, and the occurrence of defective products is minimized.

The invention claimed is:

1. A method of producing a powdered medicine multi-dose administering device which includes a container (10) capable of storing a multi-dose amount of powdered medicine and having, in the bottom portion thereof, a hole (10a) for containing a single-dose amount of the medicine and a first filter-fitting portion (11a), a first filter (12) fitted into the first filter-fitting portion, a second hole (10b) and a second filter-fitting portion (11b) provided in the bottom portion of the container, a second filter (13) coarser than the first filter (12) being fitted to the second filter-fitting portion, an inner cylinder (15) capable of being rotated between a filling position and an administering position while maintaining contact with the inner bottom surface of the container, an inner closure (19) having a center hole for rotatably supporting an upper part of the inner cylinder and for closing an opening at the upper end of the container being fitted to the inner periphery of the opening at the upper part of the container, and a nozzle (20) coupled to the upper end of the inner cylinder so as to transmit the rotation, rotatably fitted to the outer periphery of the opening at the upper part of the container and having a medicine discharge passage (20a), wherein, at the filling position, the powdered medicine in the container is supplied to the medicine-containing hole (10a) through an opening (17) in the inner cylinder and the second filter and the second hole are communicated with the medicine passage (18) in the inner cylinder and, at the administering position, the air is blown into the medicine-containing hole (10a) through the first filter, so that the medicine in the medicine-containing hole is discharged to the exterior through a medicine passage (18) of the inner cylinder and the medicine discharge passage (20a) of the nozzle;

said method of producing a powdered medicine multi-dose administering device comprising the steps of:

inserting the second filter (13) in the second filter-fitting portion (11b);

inserting the first filter (12) in the first filter-fitting portion (11a);

inserting the inner cylinder (15) in the container body (10);

filling the container with the powdered medicine;

inserting the inner closure (19) to the container and fitting it to the inner cylinder; and fitting the nozzle (20) to the container to couple it to the inner cylinder.

2. A method of producing a powdered medicine multi-dose administering device according to claim 1, wherein, in the step of inserting the first and second filters (11, 12), the container (10) is installed with its bottom portion facing upward.

3. A method of producing a powdered medicine multi-dose administering device according to claim 1, wherein in the step of inserting the first and second filters (12, 13), the insertion is conducted while applying insertion guides to the first and second filter-fitting portions (11a, 11b), respectively.

4. A method of producing a powdered medicine multi-dose administering device according to claim 1, wherein, at the time of inserting the first filter (12) in the first filter-fitting portion (11a), the up-and-down direction of the filter is confirmed; while at the time of inserting the second filter (13) in the second filter-fitting portion (11b), the up-and-down direction of the filter is not confirmed.

5. A method of producing a powdered medicine multi-dose administering device according to claim 1, wherein in inserting the first filter (12) in the first filter-fitting portion (11a), the first filter is provisionally inserted in a first step and is, then, press-inserted in a next step.

6. A method of producing a powdered medicine multi-dose administering device according to claim 1, wherein the second filter (13) is inserted in the second filter-fitting portion (11b), then the depth of insertion of the second filter is measured and the first filter (12) is press-inserted in the first filter-fitting portion (11a), then the depth of press-insertion of the first filter (12) is measured.

7. A method of producing a powdered medicine multi-dose administering device according to claim 1, wherein after the first and second filters (12, 13) have been inserted in the first and second filter-fitting portions (11a, 11b), the container (10) is turned upside down.

8. A method of producing a powdered medicine multi-dose administering device according to claim 7, wherein the steps of inserting the first and second filters (12, 13) are executed while the container (10) is being conveyed by a first conveyer, and the steps after the container (10) is turned upside down are executed while the container (10) is being conveyed by a second conveyer.

9. A method of producing a powdered medicine multi-dose administering device according to claim 8, wherein in transferring the container (10) onto the first conveyer, the position of the container (10) in the rotational direction is determined by utilizing a protrusion (14) provided at a central position on the inner bottom surface of the container.

10. A method of producing a powdered medicine multi-dose administering device according to claim 8, wherein, in transferring the container (10) onto the second conveyer, the position of the container (10) in the rotational direction is determined by utilizing the first and second filter-fitting portions (11a, 11b) that are protruding outward from the bottom portion of the container (10).

11. A method of producing a powdered medicine multi-dose administering device according to claim 8, wherein after the container (10) is transferred onto the second conveyer, the interior of the container is cleaned by injecting the compressed air into the container and sucking the air prior to inserting the inner cylinder (15) in the container.

12. A method of producing a powdered medicine multi-dose administering device according to claim 1, wherein, in inserting the inner cylinder (15) in the container, the position of the inner cylinder in the rotational direction is determined by utilizing a non-circular portion formed at a portion coupled to the nozzle at the upper end of the inner cylinder (15).

13. A method of producing a powdered medicine multi-dose administering device according to claim 1, wherein after the inner cylinder (15) is inserted in the container, the depth of insertion of the inner cylinder is measured.

14. A method of producing a powdered medicine multi-dose administering device according to claim 1, wherein, after the inner cylinder (15) is inserted in the container, the container is cleaned by supplying air therein while holding the interior of the container by the inner cylinder.

15. A method of producing a powdered medicine multi-dose administering device according to claim 1, wherein, in the step of filling the container with the powdered medicine, the container is filled with the powdered medicine through a ring-like opening between the opening at the upper end of the container and the inner cylinder (15) by utilizing a filling funnel.

16. A method of producing a powdered medicine multi-dose administering device according to claim 1, wherein, in the step of filling the container with the powdered medicine, the container is vibrated.

17. A method of producing a powdered medicine multi-dose administering device according to claim 1, wherein, in the step of inserting the inner closure (19) in the container, the inner closure is fixedly fitted to the inner periphery of the opening at the upper part of the container and, at the same time, the rotary shaft portion (15d) at the upper part of the inner cylinder is fitted to the center hole of the inner closure in a non-fixed manner.

18. A method of producing a powdered medicine multi-dose administering device according to claim 17, wherein, in the step of inserting the inner closure (19) in the container, the inner closure is provisionally inserted in the container in a first step and, then, is press-inserted in the container in a next step.

19. A method of producing a powdered medicine multi-dose administering device according to claim 18, wherein, in press-inserting the inner closure 19 in the container, the inner closure is press-inserted in the container while holding the upper end of the inner cylinder (15) that is protruded upward beyond the inner closure.

20. A method of producing a powdered medicine multi-dose administering device according to claim 18, wherein, in holding the upper end of the inner cylinder (15), the position of the inner cylinder is corrected at the same time by utilizing the noncircular shaft portion (15c) at the upper end of the inner cylinder.

21. A method of producing a powdered medicine multi-dose administering device according to claim 1, wherein, after the inner closure (19) is fitted into the container and to the inner cylinder, the depth of insertion of the inner closure is measured.

22. A method of producing a powdered medicine multi-dose administering device according to claim 20, wherein, in the step of inserting the nozzle (20) in the container, the nozzle is fitted in a non-fixed manner to the outer periphery of the opening at the upper part of the container body and, at the same time, a non-circular hole (20c) of the nozzle is coupled to the noncircular shaft portion (15c) at the upper end of the inner cylinder in a manner to transmit rotation.

23. A method of producing a powdered medicine multi-dose administering device according to claim 22, wherein, in the step of inserting the nozzle (20) in the container, a pin is inserted in the noncircular hole (20c) of the nozzle that corresponds to the noncircular portion at the upper end of the inner cylinder (15) prior to inserting the nozzle, thereby to determine the position of the nozzle in the direction of rotation.

24. A method of producing a powdered medicine multi-dose administering device according to claim 1, wherein, after the nozzle (20) is inserted in the container, the depth of insertion of the nozzle is measured.

25. A method of assembling a powdered medicine administering device which permits an inner cylinder to move between a medicine filling position and a blow-out position upon turning a nozzle, comprising the steps of:
  incorporating first and second filters (12, 13) on the outer side of a bottom portion of a container (10) with the bottom portion being positioned on the upper side, the second filter (13) being coarser than the first filter (12);
  turning the container upside-down so that the open end of the container faces upward;
  inserting the inner cylinder (15) in the container from the side of open end of the container;
  filling the container with a predetermined amount of powdered medicine from the side of open end of the container;
  securing and fitting the inner closure (19) to the open end of the container as well as to the inner cylinder so that the inner cylinder partly protrudes toward outside of the container; and
  rotatably fitting the nozzle (20) to the open end of the container while coupling it to the inner closure (19) in a manner to transmit the rotation.

26. A method of producing a powdered medicine multi-dose administering device which includes a container (10) capable of storing a multi-dose amount of powdered medicine and having, in the bottom portion thereof, a hole (10a) for containing a single-dose amount of the medicine and a first filter-fitting portion (11a), a first filter (12) fitted into the first filter-fitting portion, a second hole (10b) and a second filter-fitting portion (11b) provided in the bottom portion of the container, a second filter (13) coarser than the first filter (12) being fitted to the second filter-fitting portion, an inner cylinder (15) capable of being rotated between a filling position and an administering position while maintaining contact with the inner bottom surface of the container, an inner closure (19) having a center hole for rotatably supporting an upper part of the inner cylinder and for closing an opening at the upper end of the container being fitted to the inner periphery of the opening at the upper part of the container, and a nozzle (20) coupled to the upper end of the inner cylinder so as to transmit the rotation, rotatably fitted to the outer periphery of the opening at the upper part of the container and having a medicine discharge passage (20a), wherein, at the filling position, the powdered medicine in the container is supplied to the medicine-containing hole (10a) through an opening (17) in the inner cylinder and the second filter and the second hole are communicated with the medicine passage (18) in the inner cylinder and, at the administering position, air is blown into the medicine-containing hole (10a) through the first filter, so that the medicine in the medicine-containing hole is discharged to the exterior through the medicine passage (18) of the inner cylinder and the medicine discharge passage (20a) of the nozzle,
  said method of producing a powdered medicine multi-dose administering device comprising the steps of:
    inserting the second filter (13) in the second filter-fitting portion (11b);
    inserting the first filter (12) in the first filter-fitting portion (11a);
    inserting the inner cylinder (15) in the container body (10);
    filling the container with the powdered medicine;
    inserting the inner closure (19) to the container and fitting it to the inner cylinder;
    fitting the nozzle (20) to the container to couple it to the inner cylinder; and
    inspecting the thus obtained assembly.

27. A method of producing a powdered medicine multi-dose administering device according to claim 26, wherein in a state where the assembly is obtained, the inner cylinder (15) is set at the administering position, and the step of inspecting the assembly comprises the following sub-steps of:
  first measuring sub-step of measuring the initial load of the assembly;
  turning the nozzle (20) by a predetermined angle relative to the container body to bring the inner cylinder to the filling position;
  vibrating the assembly;

turning the nozzle in the opposite direction by a predetermined angle relative to the container body to bring the inner cylinder to the administering position;

sucking the air from the end of the nozzle (20) while injecting the compressed air through the filter so that a single-dose amount of the powdered medicine in the medicine-containing hole (10a) is injected from the nozzle; and second measuring sub-step of measuring the load of the assembly after the injection and calculating the amount of injection from the weight difference between before and after the injection; and wherein said first and second measuring sub-steps are carried out by an electronic balance provided with a windbreak.

28. A method of producing a powdered medicine multi-dose administering device according to claim 27, wherein, after the initial load of the assembly is measured, the assembly is transferred onto an index table, and the individual sub-steps in the step of inspection are executed while an index table is being turned.

29. A method of producing a powdered medicine multi-dose administering device according to claim 27, wherein a rotary cylinder is used in the foregoing two sub-steps of turning the nozzle relative to the container body, and an urethane rubber is arranged at the chuck portion of the rotary cylinder that comes into contact with the nozzle.

30. An apparatus for producing a powdered medicine multi-dose administering device which includes a container (10) capable of storing a multi-dose amount of powdered medicine and having, in the bottom portion thereof, a hole (10a) for containing a single-dose amount of the medicine and a first filter-fitting portion (11a), a first filter (12) fitted into the first filter-fitting portion, a second hole (10b) and a second filter-fitting portion (11b) provided in the bottom portion of the container, a second filter (13) coarser than the first filter (12) being fitted to the second filter-fitting portion, an inner cylinder (15) capable of being rotated between a filling position and an administering position while maintaining contact with the inner bottom surface of the container, an inner closure (19) having a center hole for rotatably supporting an upper part of the inner cylinder and for closing an opening at the upper end of the container being fitted to the inner periphery of the opening at the upper part of the container, and a nozzle (20) coupled to the upper end of the inner cylinder so as to transmit the rotation, rotatably fitted to the outer periphery of the opening at the upper part of the container and having a medicine blow-out passage (20a), wherein, at the filling position, the powdered medicine in the container is supplied to the medicine-containing hole (10a) through an opening (17) in the inner cylinder and the second filter and the second hole are communicated with the medicine passage (18) in the inner cylinder, and, at the administering position, the air is blown into the medicine-containing hole (10a) through the filter, so that the medicine in the medicine-containing hole is discharged to the exterior through the medicine passage (18) of the inner cylinder and the medicine discharge passage (20a) of the nozzle, said an apparatus for automatically producing a powdered medicine multi-dose administering device, comprising:

a production unit for inserting the first filters in the first filter-fitting portions, inserting the second filter (13) in the second filter-fitting portion (11b); inserting the inner cylinder in the container body, filling the container with the powdered medicine, fitting the inner closure to the container and to the inner cylinder, and fitting the nozzle (20) to the container while coupling it to the inner cylinder to produce an assembly; and an inspection unit for inspecting the assembly that is produced and for measuring the amount of injection of a single-dose amount of the powdered medicine.

31. A powdered medicine multi-dose administering device which includes:

a container (10) capable of storing a multi-dose amount of powdered medicine and having, in the bottom portion thereof, a first hole (10a) for containing a single-dose amount of the medicine and a filter-fitting portion (11a);

a first filter (12) fitted into the filter-fitting portion, an inner cylinder (15) capable of being rotated between a filling position and an administering position while maintaining contact with the inner bottom surface of the container;

an inner closure (19) having a center hole for rotatably supporting an upper part of the inner cylinder and for closing an opening at the upper end of the container being fitted to the inner periphery of the opening at the upper part of the container;

a nozzle (20) coupled to the upper end of the inner cylinder so as to transmit the rotation, rotatably fitted to the outer periphery of the opening at the upper part of the container and having a medicine discharge passage (20a);

a pump (21) capable of blowing air into the first hole (10a) through the first filter (12);

wherein, at the filling position, the powdered medicine in the container is supplied to the medicine-containing hole (10a) through an opening (17) in the inner cylinder, and, at the administering position, the air is blown into the medicine-containing hole (10a) through the first filter, so that the medicine in the medicine-containing hole is discharged to the exterior through a medicine passage (18) of the inner cylinder and the medicine discharge passage (20a) of the nozzle; and wherein a second hole (10b) and a second filter-fitting portion (11b) are provided in the bottom portion of the container, a second filter (13) coarser than the first filter (12) is fitted to the second filter-fitting portion, and the second filter and the second hole are communicated with the medicine passage (18) in the inner cylinder at the filling position.

32. An assembly of a powdered medicine multi-dose administering device which includes:

a container body (10) capable of storing a multi-dose amount of powdered medicine and having, in the bottom portion thereof, a first hole (10a) for containing a single-dose amount of the medicine and a filter-fitting portion (11a);

a first filter (12) fitted into the filter-fitting portion, an inner cylinder (15) capable of being rotated between a filling position and an administering position while maintaining contact with the inner bottom surface of the container;

an inner closure (19) having a center hole for rotatably supporting an upper part of the inner cylinder and for closing an opening at the upper end of the container being fitted to the inner periphery of the opening at the upper part of the container;

a nozzle (20) coupled to the upper end of the inner cylinder so as to transmit the rotation, rotatably fitted to the outer periphery of the opening at the upper part of the container and having a medicine discharge passage (20a);

wherein, at the filling position, the powdered medicine in the container is supplied to the medicine-containing hole (10a) through an opening (17) in the inner cylinder, and, at the administering position, air is blown into the medicine-containing hole (10*a*) through the first filter, so that the medicine in the medicine-containing hole is discharged to the exterior through a medicine passage (18) of the inner cylinder and the medicine discharge passage (20*a*) of the nozzle; and wherein a second hole (10*b*) and a second filter-fitting portion (11*b*) are provided in the bottom portion of the container, a second filter (13) coarser than the first filter (12) is fitted to the second filter-fitting portion, and the second filter and the second hole are communicated with the medicine passage (18) in the inner cylinder at the filling position.

* * * * *

UNITED STATES PATENT AND TRADEMARK OFFICE
CERTIFICATE OF CORRECTION

PATENT NO. : 7,611,078 B2
APPLICATION NO. : 10/489662
DATED : November 3, 2009
INVENTOR(S) : Zaima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1437 days.

Signed and Sealed this

Twelfth Day of October, 2010

David J. Kappos
*Director of the United States Patent and Trademark Office*